United States Patent [19]

Salo

[11] Patent Number: 5,700,283
[45] Date of Patent: Dec. 23, 1997

[54] METHOD AND APPARATUS FOR PACING PATIENTS WITH SEVERE CONGESTIVE HEART FAILURE

[75] Inventor: Rodney W. Salo, Fridley, Minn.

[73] Assignee: Cardiac Pacemakers, Inc., St. Paul, Minn.

[21] Appl. No.: 754,932

[22] Filed: Nov. 25, 1996

[51] Int. Cl.$^6$ .......................... A61N 1/365; A61N 1/368; A61N 1/362
[52] U.S. Cl. .................. 607/17; 607/18; 607/23; 607/25
[58] Field of Search .................. 607/17, 18, 23, 607/25

[56] References Cited

U.S. PATENT DOCUMENTS

| | | | |
|---|---|---|---|
| 4,730,619 | 3/1988 | Koning et al. | 607/23 |
| 5,334,222 | 8/1994 | Salo et al. | 607/17 |
| 5,487,752 | 1/1996 | Salo et al. | 607/17 |
| 5,540,727 | 7/1996 | Tockman et al. | 607/17 |
| 5,549,650 | 8/1996 | Bornzin et al. | 607/24 |

OTHER PUBLICATIONS

Weissler et al., "6–Systolic Time Intervals", *Non–Invasive Cardiology*, Chapter 6, Grune & Stratton, ©1974, pp. 302–306.

Linde C, Gadler F, Edner M, Nordlander R, Rosenquist M: (abstract) Is DDD pacing with short AV delay a beneficial treatment in patients with severe heart failure? PACE 1994; 17(Part II): 744.

Foster AH, McLaughlin JS, Fisher ML: (abstract) Improved hemodynamics with biventricular pacing. J Am Coll Cardiol 1994; 23 (Supp A); 156A.

Bakker PJ, Meijburg H, de Jonge N, van Mechelen R, Wittkampf, Mower M, Thomas A: (abstract) Beneficial effects of biventricular pacing in congestive heart failure. PACE 1994; 17(Part II): 820.

Hochleitner M, Hörtngal H, Fridrich L, et al: Long–term efficacy of physiologic dual chamber pacing in the treatment of end–stage idiopathic dilated cardiomyopathy. Am J Cardiol 1992; 70: 1320.

Auricchio A, Sommariva L, Salo RW, et al: Improvement of cardiac function with severe congestive heart failure and coronary artery disease with shortened AV delay. PACE 1993; 16: 2034.

Feliciano Z, Fisher ML, Corretti MC, Gottlieb SS, Gold MR: (abstract) Acute hemodynamic effect of AV delay in patients with congestive heart failure. J Am Coll Cardiol 1994; 23 (Supp A): 349A.

Nishimura Ra, Hayes DL, Holmes DR, et al.: Mechanism of hemodynamic improvement by dual–chamber pacing for severe left ventricular dysfunction: An acute doppler and catheterization hemodynamic study. J Am Coll Cardiol 1995; 25: 281–8.

Brecker SJ, Xiao HB, Sparrow J, Gibson DG: Effect of dual–chamber pacing with short atrioventricular delay in dilated cardiomyopathy. Lancet 1992; 340: 1308–12.

Freedman RA, Yock PG, Echt D, Popp RL: Effect of variation in PQ interval on patterns of atrioventricular valve motion and flow in patients with normal ventricular function. J Am Coll Cardiol 1986; 7: 595–602.

*Primary Examiner*—Marvin M. Lateef
*Assistant Examiner*—Carl H. Layno
*Attorney, Agent, or Firm*—Haugen and Nikolai, P.A.

[57] ABSTRACT

An implantable cardiac pacemaker especially designed for treatment of CHF includes an accelerometer for sensing heart sounds and processing circuitry for deriving from the heart sound information the mechanical AV delay of the patient's heart. The pacemaker's applied AV delay is then adjusted until the measured mechanical AV delay falls in a range of between 180 ms and 250 ms. Further optimization of the heart as a pump can then be achieved by incrementally adjusting the pacemaker's applied AV delay interval until a point is reached where a measure of cardiac performance such as aortic pulse pressure is optimized.

4 Claims, 5 Drawing Sheets

METHOD AND APPARATUS FOR PACING PATIENTS WITH SEVERE CONGESTIVE HEART FAILURE

BACKGROUND OF THE INVENTION

I. Field of the Invention

This invention relates generally to cardiac rhythm management, and more particularly to a pacing system and method for treating patients having congestive heart failure.

II. Discussion of the Prior Art

Despite major advances in the prevention and treatment of cardiovascular diseases, as is evident from the substantial decline in mortality due to acute myocardial infarction and strokes in the United States and in most European countries, national statistics indicate that the incidents and prevalence of congestive heart failure (CHF) have been increasing in recent years. Patients with CHF have an impaired quality of life and a shortened life expectation. Although angiotensin-converting enzymes (ACE) inhibitors have been shown to modify the natural course of CHF reducing the mortality rate by 30%, the underlying disease continues to evolve, becoming progressively unresponsive to common drugs, until eventually intravenous inotropic support is needed. At end-stage, heart transplantation becomes the only therapeutic option.

Hochleitner et al., in a paper entitled "Long-Term Efficacy of Physiologic Dual Chamber Pacing in the Treatment of End-stage Idiopathic Dilated Cardiomyopathy", Am J Cardiol 1992; 70:1320 reported the long-term beneficial effects of a dual chamber pacemaker using a short atrioventricular delay (AV delay) of 100 ms in the treatment of end-stage idiopathic dilated cardiomyopathy in 16 patients without usual pacing indications in whom conventional therapy failed. There was a striking improvement in the symptoms, which included severe dyspnea at rest and pulmonary congestion, as well as a significant decrease in the New York Heart Association functional class. Similarly, the present applicants, in their paper entitled "Improvement of Cardiac Function With Severe Congestive Heart Failure and Coronary Artery Disease With Shortened AV delay"; PACE 1993; 16:20–34, demonstrated significant clinical improvement in ischemic dilated cardiomyopathy patients with atrial sensed ventricular stimulation (VDD) pacing and shortened AV delay. In conducting the study which served as a basis for their report, the AV delay selection was based on acutely acquired hemodynamic and doppler information.

Studies performed by Linde et al. (PACE 1994; 17:744) and Feliciano et al. (J Am Coll Cardiol 1994; 23:349A) failed to demonstrate statistically significant improvements tributable to pacing either in acutely acquired hemodynamic parameters or in the functional status of patients. However, it is interesting to note that individual patients in each reported series were found to have benefited from dual chamber pacemaker implantation with shortened AV delay. More recently, Foster et al. (J Am Coll Cardiol 1994; 23:156A) and Bakker et al. (PACE 1994; 17 (Part II):820) using simultaneous left and right ventricular pacing (biventricular pacing) have shown dramatic hemodynamic and clinical improvement in acute testing and short-term follow-up, respectively. This apparently contradictory data concerning the benefit of ordinary dual chamber or biventricular stimulation in patients with congestive heart failure is believed to arise from disparate methods and patient selection.

SUMMARY OF THE INVENTION

Acute pacing studies conducted on CHF patients have led us to conclude that pacing benefits selected patients, particularly those with conduction defects. The stimulation site (either right ventricle, left ventricle or both ventricles) and the programmed AV delay were varied while measuring cardiac performance and the heart's mechanical AV delay (MAVD). It was concluded that most CHF patients have improved hemodynamic performance when the MAVD is made to fall in the range of from 180 to 250 milliseconds.

However, the relationship between programmed electrical AV delay and MAVD cannot be predicted for individual patients. In general, the two intervals are linearly related with a slope of approximately 1.0 but the offset (y intercept) between the two varies with pacing mode and is currently unpredictable. Therefore, to guarantee that the MAVD falls within the optimum range, it is necessary to measure the MAVD while pacing at a known programmed AV delay and then adjust the programmed AV delay to move the MAVD into the desired range.

Based upon these findings, we have developed a method of treating congestive heart failure that comprises the steps of providing a dual chamber cardiac pacemaker that includes a means for sensing the onset of atrial ejection and the onset of aortic ejection and which has a programmable AV delay parameter between a sensed atrial beat and the generation of a next succeeding ventricular stimulating pulse. The ventricular stimulating pulses are applied to the patient's heart at a known programmed electrical AV delay and the MAVD is measured. Based on the measured MAVD value, the programmed electrical AV delay is modified to bring the MAVD into the optimum range of approximately 180 to 250 milliseconds (since a MAVD is 215 milliseconds falls in the middle of the range, this figure would be a likely target and is used in the following equation). For example the new programmed electrical AV delay can be computed by:

Programmed AV Delay (new)=Programmed AV Delay (original)+ [215 msec−MAVD (original)].

The above computation can either be carried out by the operator and the new AV delay programmed into the device by an external programmer or the computation and reprogramming may be carried out internally by the microprocessor used in the pacing device without operation intervention.

The hemodynamic performance of the heart can then be further optimized by incrementally varying the programmable AV delay parameter over a limited range of MAVD near that predicted by the above equation while monitoring a measure of cardiac performance such as aortic pulse pressure and setting the AV delay parameter at a value where the particular measure of cardiac performance is optimized.

A pacemaker device for use in treating CHF will thus include a means for sensing atrial depolarization signals, means for sensing ventricular depolarization signals, means for generating ventricular stimulating signals and will have an externally or internally programmable AV delay between the sensing of an atrial depolarization signal and the generation of a stimulating ventricular pulse. A sensor to detect atrial and left and/or right ventricular ejection, such as an accelerometer for detecting cardiac acoustic activity is necessary to measure MAVD and to determine the correct programmed AV delay to apply to the heart to generate a MAVD in the range of 180–250 msec. Of course, it is also possible to use external equipment, such as an echocardiography system, to determine MAVD and then to use this information to reprogram the AV delay with an external programmer as discussed previously.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
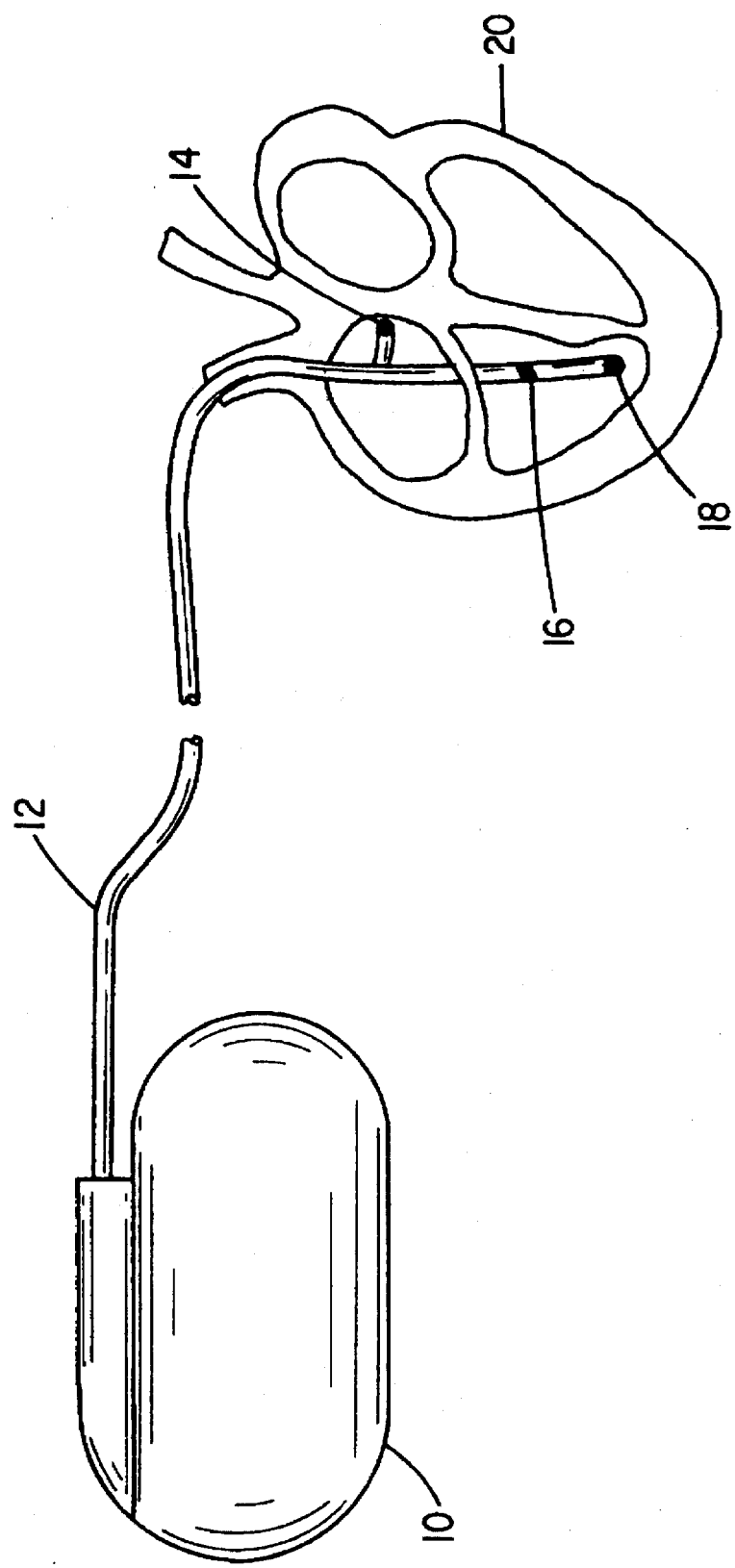
FIG. 1 illustrates a dual chamber pacemaker and a pacemaker lead connecting it to pacing and sensing electrodes located in a heart.

Referring to FIG. 1, there is shown a dual chamber pacemaker 10 having one or more leads, as at 12, connecting the pacemaker to an atrial sensing electrode 14 located in the right atrium, a ventricular sensing electrode 16 located in the right ventricle and a ventricular pacing electrode 18 located at the right ventricular apex of the heart 20.

Figure 2:
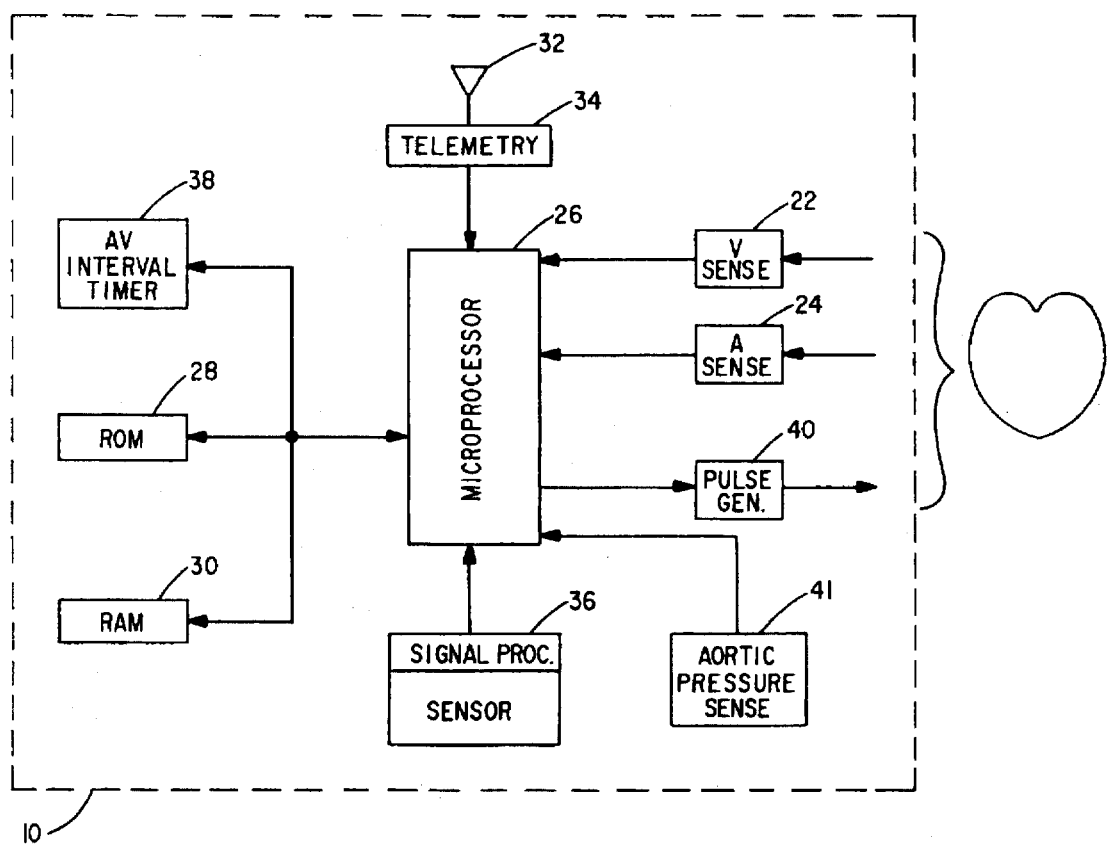
FIG. 2 is a block diagram representation of the pacemaker of FIG. 1.

FIG. 2 is a block diagram representation of the circuitry contained within the housing or can of the pacemaker 10. Signals picked up by the ventricular sensing electrode 16 are applied to a ventricular sense amplifier 22 which enhances the spontaneously occurring R-wave signals produced upon ventricular depolarization. Likewise, an atrial sense amplifier 24 amplifies and signal processes signals picked up by the atrial electrode 14 corresponding to atrial depolarization signals (P-waves). The outputs from the V-sense circuit 22 and the A-sense circuit 24 are applied as inputs to a microprocessor-based controller 26.

The microprocessor-based controller 26 has associated with it a ROM memory which stores a program of instructions and a RAM memory 30 for storing various operands and externally programmable parameters. Such externally programmable parameters may be telemetered to an implanted pacemaker via an antenna 32 and conventional telemetry circuits 34 well known to those skilled in the art.

Figure 3:
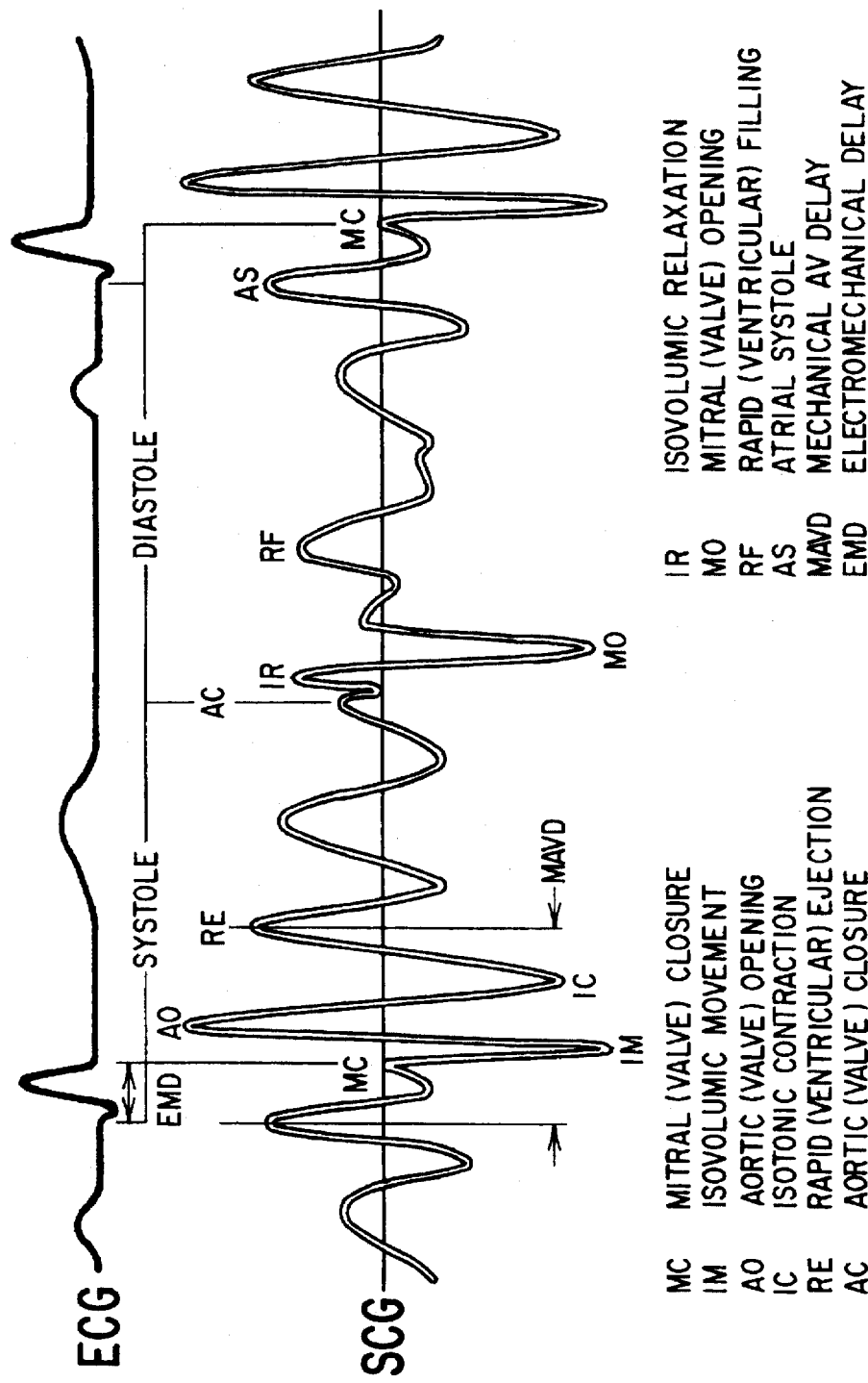
FIG. 3 is a seismocardiogram (SCG) showing the time of occurrence of various cardiac events and in timewise alignment with the ECG waveform.

In accordance with the present invention, there is also provided a sensor circuit 36 contained within the can or housing of the pacemaker 10 and which sensor also provides an input to the microprocessor-based controller 26. In the preferred embodiment of the present invention, the sensor may be an accelerometer-type transducer capable of detecting heart sounds associated with the beginning of atrial ejection when the atrial ventricular valves open to allow blood to pour from the atria into the ventricles as well as the beginning of aortic ejection when the aortic valve opens to allow the contents of the left ventricle to be ejected to the aorta. Referring to the graph of FIG. 3 which shows a typical signal obtained from an accelerometer due to the various events in a cardiac cycle, the left heart mechanical AV delay (MAVD) is the time interval between the beginning of atrial ejection and the start of ventricular ejection.

The pacemaker 10 of FIG. 2 further includes an AV interval timer whose initial count value is programmable, via the telemetry link 32, 34, and is loaded into the timer 38 upon the occurrence of an atrial depolarization signal. The microprocessor provides regularly occurring clock pulses to decrement the AV interval timer 38 and when the count reaches 0, the microprocessor 26 issues a command to the pulse generator 40 to send a ventricular stimulating pulse to the heart, via electrode 18. Finally, a suitable transducer for measuring aortic pulse pressure may be incorporated into the lead 12 for implementing the sensor 41 in FIG. 2.

A major clinical impact of slowed interatrial conduction is a decrease in left heart AV delay. Pacing the atrium, which results in increased interatrial conduction time, exacerbates this effect. We have found that appropriate selection of paced AV delay is critical in that inappropriate short values could result in a very short left heart mechanical AV delay with resultant depression of ventricular function. Unless intra-atrial, inter-atrial, intraventricular and interventricular timing, as well as associated electromechanical delays, are well defined, it is difficult to predict the effect of pacing on patients with CHF. As part of a study leading to the present invention, acute hemodynamic testing was performed on a number of patients with severely diseased ventricles in order to optimize the atrioventricular delay. We determined that VDD stimulation is more effective than DDD stimulation and that the mechanical AV interval is a more definitive parameter than the heart's electrical AV interval when optimizing cardiac function. In that there are complex electrical and mechanical timing relationships among the four chambers of the heart, it is difficult to predict mechanical atrio-ventricular timing from the applied AV delay or the measured electrical AV delay. Instead, in carrying out the method of the present invention, the pacemaker 10 with the accelerometer sensor 36 can be used to directly measure MAVD which is found to be more directly related to cardiac function than the electrical AV delay. In most instances, the MAVD for the patients tested fell in the range of from 180 to 250 ms during sinus rhythm. We have concluded that patients with MAVD outside of this normal range when in sinus rhythm will benefit from pacing so as to restore a more normal MAVD.

Figure 4:
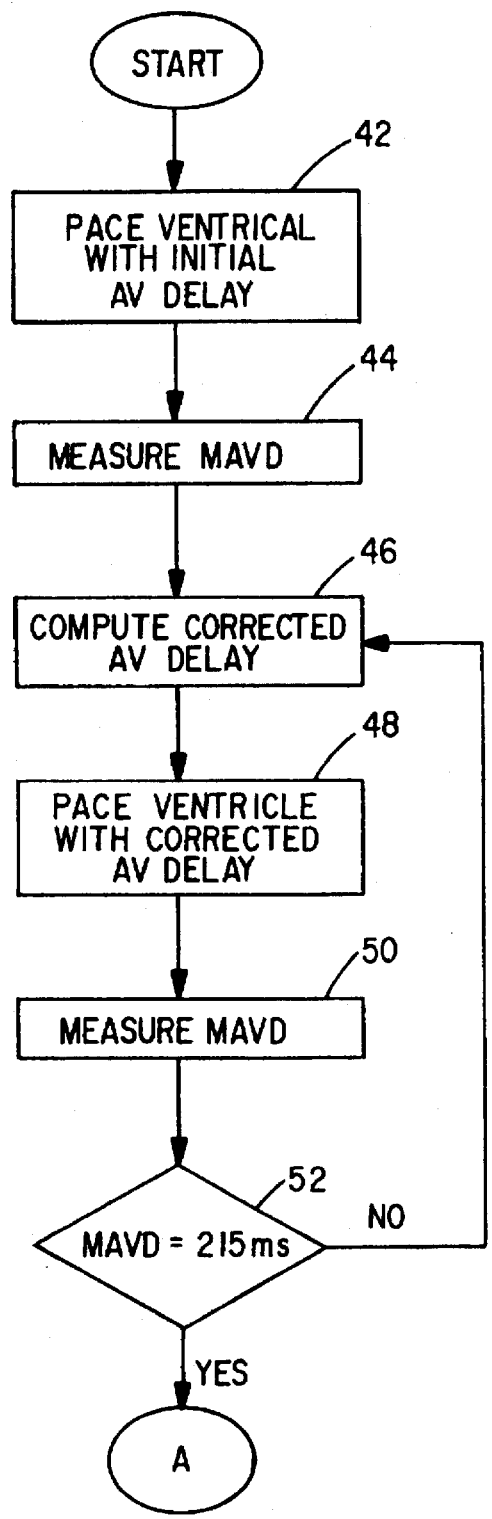
FIGS. 4(A) and 4(B) comprise a software flow diagram for the algorithm employed in pacing the heart for optimizing hemodynamic performance for patients afflicted with congestive heart failure.

Referring to FIG. 4, there is shown a software flow diagram which illustrates the algorithm for setting an appropriate AV delay for a dual chamber pacer based upon a sensed mechanical AV delay. In carrying out the method, the physician may enter an initial AV delay parameter into the pacemaker (block 42). In carrying out the method, the physician may enter an initial AV delay value via the external programmer or, alternatively, a preprogrammed default value may be utilized in pacing the ventricle with an initial AV delay value (block 42). The accelerometer sensor 36 and associated signal processing circuitry provides a heart sound envelope to the microprocessor 26 from which MAVD can be measured (block 44). In this regard, reference is made to the waveform of FIG. 3 for the definition of the MAVD interval.

Next, the microprocessor 26 computes a corrected AV delay value (block 46) using the equation:

AV Delay (new)=AV Delay (initial)+[215 ms−MAVD (initial)].

The ventricle is then paced with the newly computed AV delay value (block 48) and again the MAVD is measured (block 50), but with the new AV delay being used. A test is then made to determine whether measured MAVD is, say 215 ms (block 52). If not, steps 46–50 are repeated until the test at block 52 is true.

Figure 4B:
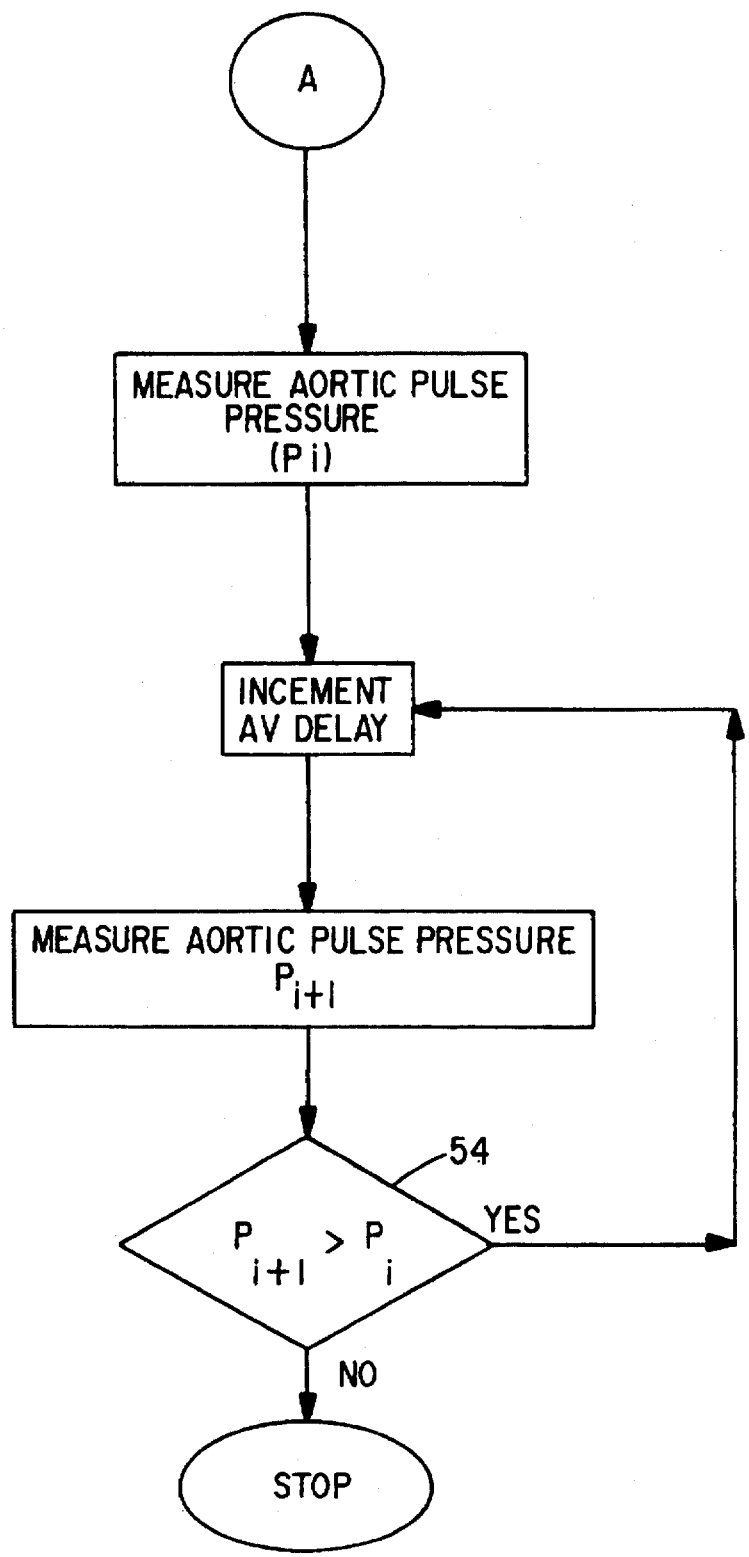

While not essential to the practice of the method of the present invention, if desired, further optimization can then take place by following the algorithm of FIG. 4(B). By incrementally adjusting the AV delay and determining on each iteration whether aortic pulse pressure increases the AV delay interval marches forward toward an optimum. So long as the incrementation of AV delay results in an increase in aortic pulse pressure, the process continues. However, when the test at block 54 shows no attendant increase in aortic pulse pressure, the AV delay is not further incremented. If the further optimization steps of FIG. 4(B) are employed, then it is advisable that a number less than 215 ms be used in the test block 52 in FIG. 4(A). For example, a value of 180 ms may be chosen.

A further variation to the optimization method of the present invention in treating CHF resides in the recognition that instead of a separate sensor for determining maximum aortic pressure in further optimizing AV delay after forcing the MAVD to be in a correct range of between 180 ms and 250 ms, the same accelerometer used for MAVD optimization can be used. Specifically, the accelerometer signal can be integrated on a beat-by-beat basis while modifying the AV delay parameter to minimize the integrated value. In carrying out the signal integration, the accelerometer output may first be high-pass filtered using a cut-off frequency in the range of from 0.1 Hz to 0.5 Hz to remove baseline variations due to respiratory activity, etc. The resulting filter output is then rectified and integrated over the heart beat interval to obtain a single value representation of the beat. Thus, the patient will be paced such that the heart's mechanical AV delay will be in a range found by tests on a patient population to be most beneficial for those patients suffering CHF and at an AV delay value assuring maximum aortic pulse pressure or minimum integrated accelerometer signal.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method of treating patients having congestive heart failure comprising the steps of:

(a) providing a dual-chamber cardiac pacemaker of the type having means for sensing atrial depolarization signals, means for sensing ventricular depolarization signals, means for generating ventricular stimulating signals, an accelerometer for sensing heart sounds and a programmable AV delay interval between the sensing of an atrial depolarizing signal and the sensing of a next succeeding ventricular depolarizing signal;

(b) deriving from the heart sounds a measure of an interval between the onset of atrial ejection and of aortic ejection in the patient's heart; and (c) adjusting the AV delay interval of the pacemaker until the interval measured in step (b) falls in the range of from about 180 ms to 250 ms.

2. The method as in claim 1 and further including the step of incrementally adjusting the programmable AV delay interval while measuring pulse pressure and for fixing the AV delay interval at a value corresponding to a maximum measured pulse pressure value.

3. A pacemaker for use in treating patients having congestive heart failure, comprising in combination:

(a) means for sensing atrial events;

(b) means for sensing ventricular events;

(c) means for generating ventricular stimulating pulses following a programmed AV delay interval;

(d) means in said pacemaker for determining a mechanical AV delay of a patient's heart; and (e) means for adaptively and incrementally setting the programmed AV delay interval until the mechanical AV delay interval falls in a range of from about 180 ms to about 250 ms.

4. A method of treating patients having congestive heart failure comprising the steps of:

(a) providing a dual-chamber cardiac pacemaker of the type having means for sensing atrial depolarization signals, means for sensing ventricular depolarization signals, means for generating ventricular stimulating signals, an accelerometer for sensing heart sounds and a programmable AV delay interval between the sensing of an atrial depolarizing signal and the sensing of a next succeeding ventricular depolarizing signal;

(b) obtaining from the accelerometer an integrated value of the heart sounds corresponding to total accelerometer energy; and (c) adjusting the AV delay interval of the pacemaker until the total accelerometer energy is a minimum.

* * * * *